United States Patent [19]

Benford

[11] Patent Number: 5,110,593

[45] Date of Patent: May 5, 1992

[54] IRRADICATION AND TREATMENT OF DIAPER DERMATITIS AND RELATED SKIN DISORDERS

[76] Inventor: M. Sue Benford, 6065 Frantz Rd., Ste. 205, Dublin, Ohio 43017-4020

[21] Appl. No.: 612,567

[22] Filed: Nov. 13, 1990

[51] Int. Cl.$^5$ .................................................. A61K 7/00
[52] U.S. Cl. ............................................ 424/401; 424/69; 514/865
[58] Field of Search ..................... 424/401, 69, 404; 514/941, 827, 828, 865

[56] References Cited

U.S. PATENT DOCUMENTS

| | | | |
|---|---|---|---|
| 3,567,820 | 3/1971 | Sperti | 424/79 |
| 4,034,077 | 7/1977 | Hill et al. | 424/69 |
| 4,272,514 | 6/1981 | Spence | 524/35 |
| 4,382,919 | 5/1983 | Alonso et al. | 424/69 |
| 4,474,912 | 10/1984 | Ozmeral | 514/941 |
| 4,556,560 | 12/1985 | Buckingham | 424/641 |
| 4,678,664 | 7/1987 | Schmolka | 514/563 |

OTHER PUBLICATIONS

Minnich, S. et al., "Effects of Oxyquinoline Ointment on Diaper Dermatitis" *Dermatology Nursing.* vol. 3, No. 1, Feb., 1991, pp. 25-28.

Primary Examiner—Thurman K. Page
Assistant Examiner—D. Colucci
Attorney, Agent, or Firm—Francis T. Kremblas, Jr.

[57] ABSTRACT

A method and compositions for the irradication and treatment of diaper dermatitis and related skin disorders whereby the skin is first cleansed with a non-irritating agent. The cleansed area is then treated with a specially formulated topical ointment which contains at a minimum, but is not limited to, a skin conditioning agent, a barrier agent, and an antimicrobial agent combined with other vehicles which are chemically capable of ensuring delivery of the above agents in, at least minimum inhibitory concentration.

3 Claims, 2 Drawing Sheets

```
RATING "A":   Skin completely free of rash.
RATING "B":   Skin slightly pink.
RATING "C":   Skin pink with pimply areas.
RATING "D":   Skin inflamed with pimply areas.
RATING "E":   Skin eroded and/or blistery.
```

RATING SCALE USED TO ASSESS DIAPER DERMATITIS PRESENCE AND SEVERITY.

PROPORTIONS OF INFANTS SHOWING IMPROVEMENT IN SEVERITY OF DIAPER DERMATITIS FOR THE TREATMENT GROUP AND COMBINED CONTROL GROUP (BOTH DESITIN AND A & D OINTMENT USERS).

RATING "A": Skin completely free of rash.

RATING "B": Skin slightly pink.

RATING "C": Skin pink with pimply areas.

RATING "D": Skin inflamed with pimply areas.

RATING "E": Skin eroded and/or blistery.

FIGURE 1: RATING SCALE USED TO ASSESS DIAPER DERMATITIS PRESENCE AND SEVERITY.

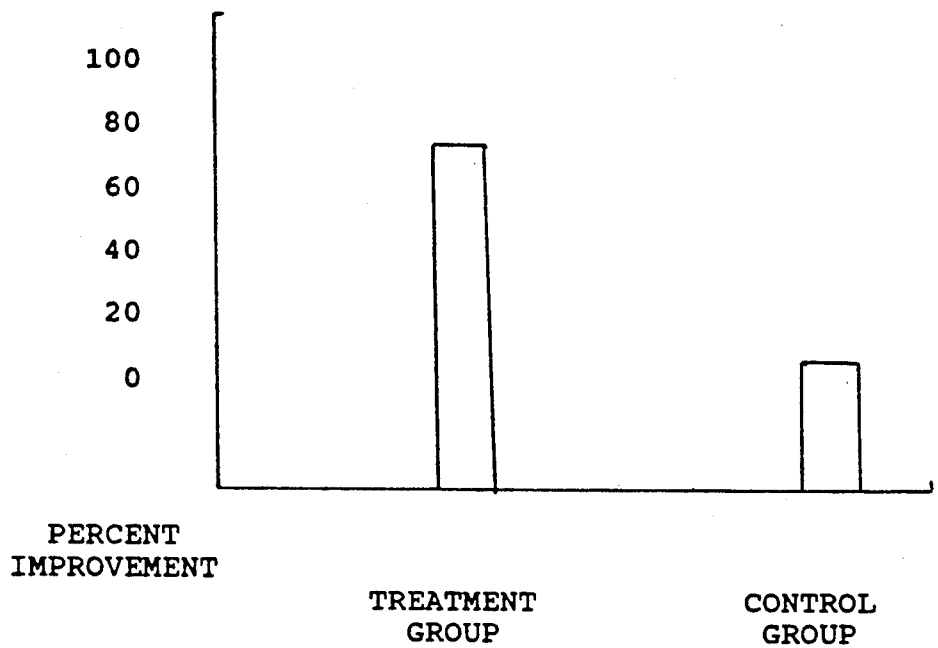
FIGURE 2: PROPORTIONS OF INFANTS SHOWING IMPROVEMENT IN SEVERITY OF DIAPER DERMATITIS FOR THE TREATMENT GROUP AND COMBINED CONTROL GROUP (BOTH *DESITIN* AND *A & D OINTMENT* USERS).

IRRADICATION AND TREATMENT OF DIAPER DERMATITIS AND RELATED SKIN DISORDERS

BACKGROUND

1. Field of Invention

This invention relates to methods and compositions for the irradication and treatment of diaper rash and related microbe-compounded diaper dermatitis.

2. Description of Prior Art

Diaper dermatitis, commonly referred to as diaper rash, is a form of irritation and inflammation that occurs in the area covered by a diaper. Although it is often dismissed by mothers or physicians as a minor problem, diaper dermatitis can have serious secondary sequela. If left untreated, diaper dermatitis can cause masceration of the skin leading to infections, trauma, and systemic disease.

"The only children who never have diaper dermatitis are those who never wear diapers" (Mantel et.al.,1980). This extremely common skin disorder is not only one of the most prevalent among infants and young children, but one of the most irritating, painful, and troublesome conditions facing babies and their mothers.

The precise prevalence of infants who suffer from diaper dermatitis is unknown. Several studies (Leyden, 1986) estimate that approximately 10% of infants between the ages of 0 to 2 years will develop diaper dermatitis although this is considered a gross underestimation. The peak incidence occurs in the 7 to 9 month age group. The U.S. Department of Health and Human Services has indicated that diaper dermatitis itself accounted for 97 visits to a physician for every 1000 infants in the United States between the ages of 0 to 2 years of age (DHHS, 1978). As most cases of diaper dermatitis are treated with over-the-counter (OTC) products, this statistic most likely reflects only the most severe cases which required more vigorous treatment.

Other data demonstrate that infants being treated for otitis media (ear infections) with antibiotics (e.g. Amoxicillin) were found to be at higher risk for diaper dermatitis compounded by a fungal infection such as *Candida albicans* (Honig et.al., 1988). Although infants who were breastfed had a lower prevalence and severity of diaper dermatitis (Benjamin, 1987; Berg, 1987), many infants and young children are not breastfed for long periods of time and/or are placed on supplemental oral feedings.

It is generally accepted that true diaper rash begins as a contact irritant dermatitis. The irritation from simple diaper dermatitis results from constant exposure of weakened or immature skin to urine or feces or both. The most commonly accepted list of factors linked to diaper dermatitis include ammonia, bacteria, the biproducts of bacterial action, urine pH, *Candida albicans* and moisture (Berg, 1987). In addition, the use of commercially available perineal cleansing wipes that contain alcohol and/or fragrances only serve to further irritate already exposed and compromised skin tissue.

Attempts to irradicate diaper dermatitis have heretofore been exclusively directed toward counteracting suspected causes of dermatitis by utilizing compositions which:

1. Promote dryness; or,
2. Provide barriers in the forms of zinc oxide, petrolatum-based substances, and lipase-inhibiting agents such as zinc chloride; or,
3. contain anti-inflammatory steroidal preparations.

Up until the present time, the treatments used for the alleviation of diaper dermatitis have focused almost exclusively on providing a barrier against common irritants. The action of these commonly used preparations is to protect the infant's sensitive skin from deterioration. Unfortunately, these preparations do little to nothing to stop the further breakdown of the skin once a full blown case of diaper dermatitis is evidenced. In fact, many pediatricians have observed that once a case of diaper dermatitis has begun, the use of air occlusive (e.g. barrier types) ointments and creams hinders the healing process (Mantel et.al.,1980).

One example of a popular OTC diaper dermatitis treatment which employs a barrier method is Desitin ® ointment, a product of Pfizer, Inc. It contains two of the common barrier substances (zinc oxide and petrolatum) and additionally contains two common skin conditioning agents (cod liver oil and lanolin). In a recent study (to be described in detail later in this document), Desitin ® ointment was utilized as one of the treatments under study and found statistically inferior to other products.

Recent research indicates that there is a significant correlation between the existence of bacteria and yeast in an infant's perineal area and the presence of diaper dermatitis. The upsurge in physician use of antibiotics to treat infants with ear infections has been linked to a new variety of diaper dermatitis that is compounded by bacteria and yeast (fungus). Thus, the use of currently available barrier methods in reusable tubes and/or containers is no longer effective in treating the vast majority of diaper dermatitis occurrences and could possibly worsen a dermatitis because they inhibit the healing process and subject the baby to repeated exposure to a contaminated product. In addition, the use of barrier method agents that are packaged in reusable containers makes transport of offending microbes from one infant to another a likely possibility.

It is apparent from the above discussion that diaper dermatitis can be a very troublesome ailment for the infant and young child. While there are over-the-counter products available that purport to be effective in the treatment of diaper dermatitis, most of these products are considered ineffective because they 1. are only effective when used in the prevention of diaper dermatitis, not the treatment;
2. are of little value once the infant's skin has broken down and diaper dermatitis is evidenced;
3. are ineffective in combating a diaper dermatitis which is compounded by the presences of bacteria and/or fungus;
4. are frequently dispensed in multi-dose, reusable containers which render the product subject to contamination and could potentially worsen an existing case of diaper dermatitis; and,
5. are rarely used in conjunction with an effective cleansing methodology. In fact, it is extremely difficult to cleanse the infant's skin once these products have been applied.

OBJECTS AND ADVANTAGES

Accordingly, there are many objects and advantages to the current methods and compositions of this invention including:

1. to provide a composition which is effective in the treatment of diaper dermatitis as demonstrated in a relevant clinical study (to be discussed later in this application);
2. to provide a composition which is effective as, but not limited solely to, a barrier against common irritants;
3. to provide a composition which is effective as, but not limited solely to, a skin conditioning agent;
4. to provide a composition which is effective in the treatment of diaper dermatitis which is complicated by bacteria and or yeast infections;
5. to provide a method for more effective treatment of diaper dermatitis which includes proper cleansing with a specific type of cleansing agent followed by the application of an effective composition; and,
6. to provide a method for dispensing said compound in such a manner as to eliminate the potential for product contamination.

PERTINENT DEFINITIONS PERTAINING TO THE INVENTION

The following terms are germane to the understanding of this patent application and will be defined in the following discussion.

By the term "affected area", as used herein, is meant the area of human skin which is presently exhibiting any of the described levels of diaper dermatitis or related skin disorder. The term will also include the area immediately proximate to the described area. The term describes the area in which treatment and irradication is desired.

By the term "single-dose application", used herein is meant a container or other such holding mechanism that contains the amount of composition required for only one topical application of a diaper dermatitis composition to be applied to the affected area at a given time. Said container is immediately disposed of following the application.

By the term "safe and effective microbial agent", as used herein is meant a chemical agent which will provide inhibition or inactivation of microorganisms necessary for the successful treatment of diaper dermatitis compounded by the presence of bacteria or fungus. Additionally, the agent must demonstrate a reasonable benefit/risk ratio attended with any accepted therapeutic treatment.

By the term "antimicrobial agent", as used herein is meant that the compound modified by this term demonstrates the ability to reduce, inhibit, or stop the growth and/or activity of microorganisms known to compound diaper dermatitis and related skin disorders.

By the term "effective amount of non-irritating skin cleansing agent", as used herein is meant an amount of cleansing agent which will aid in removing body waste and other irritants without itself causing undue irritation.

BRIEF DESCRIPTION OF THE DRAWINGS

FIG. 1 is a rating scale used to assess diaper dermatitis;

FIG 2 is the proportion of infants showing an improvement.

DESCRIPTION OF THE INVENTION

The methods and compositions of the present invention relate to the treatment and irradication of diaper dermatitis and related skin disorders caused by prolonged exposure to skin tissue irritants with potential bacterial and fungal complications. The methods and compositions of this invention require, at a minimum, but are not limited to the following:

1. as the initial step in the method, an effective amount of non-irritating skin cleansing agent applied to the affected area with either a disposable or reusable wipe, cloth, or other such vehicle; followed by:
2. a safe and effective amount of pharmaceutically-acceptable antimicrobial agent such as, but not limited to oxyquinoline, which, when topically applied, is effective in inhibiting the growth of microbes found to compound simple irritant dermatitis; and
3. a barrier-type pharmaceutically-acceptable agent such as, but not limited to petrolatum, which is capable of protecting the skin against irritants; and,
4. a skin-conditioning pharmaceutically-acceptable agent, such as, but not limited to lanolin, which is capable of providing appropriate nourishment for the skin; and,
5. said agents described above in #2, 3, and 4, are combined with a chemical vehicle which is capable of delivering said agents to the applied area of at least said agents' minimum inhibitory concentration; and,
6. the delivery of the above described composition to the affected area from a single unit-dose application that is disposed of following administration of said treatment.

The composition of this invention is not limited to the above agents and may additionally employ other optional pharmaceutically-accepted components which reduce skin irritation, act as lipase-inhibiting agents, act as anti-inflammatory agents, or improve the cosmetic acceptability of the formulation.

COMPONENTS OF INVENTION: NON-IRRITATING CLEANSING AGENT

The diapered areas of an infant or young child is constantly exposed to a variety of irritants ranging from trapped moisture, heat, and even potentially-harmful chemical substances. Diaper dermatitis that develops from exposure to these irritants is a troublesome, distressing problem. Left unattended, a dermatitis can quickly spread throughout the diapered area as it progresses from macules and papules to eroded, or crusted lesions (Scipien, 1974).

Infants are especially prone to irritant exposure and subsequent infection due to their highly permeable epidermis which results from an immature stratum corneum. Chemical and physical insults, such as ammonia, alcohol, commercially-used fragrance, and friction, decrease the ability of the epidermis to maintain the integrity of the stratum corneum resulting in the development of cutaneous lesions and potentially severe skin breakdown.

The methods of this invention include as the initial step, the use of an effective amount of non-irritating skin cleansing agent for the gentle cleansing of the diapered area of the infant prior to the topical application of the single-dose composition heretofore mentioned. No other diaper dermatitis remedy or treatment protocol specifies that cleansing is an essential component of the treatment of the disorder and includes this in combination with the secondary intervention of a single-dose antimicrobial topical application.

COMPONENTS OF INVENTION; CHEMICAL FORMULATION

An integral component of the composition of this invention is the application of a topical ointment which contains, but is not limited to the following ingredients:

| | |
|---|---|
| Petrolatum | 49.00% |
| Lanolin | 15.50% |
| Water | |
| Beeswax | |
| Sodium Borate | |
| Lanolin Alcohols | |
| Methyl Salicylate | |
| Sorbitan Sesquioleate | |
| Methylparaben | |
| Oxyquinoline | 0.22% |
| Propylparaben | |
| Trisodium HESTA | |

At this time, the composition is currently referred to as Bottom Better TM and will soon be available for commercial distribution. However, dispensing of the above described formulation may not be limited to the aforementioned product name.

It is important to note that the above mentioned chemical agents, when combined in the above mentioned quantities (but not limited to this formulation), is in compliance with the most recent Food and Drug Administration (FDA) guidelines for OTC diaper dermatitis skin care treatments (Dept. of Health & Human Services, June 1990). Additionally, there are currently NO over-the-counter diaper rash treatments which employ the aforementioned combination of ingredients in the quantities listed. The antimicrobial agents of said composition of the present invention are used at levels which are both safe and effective when topically applied to the affected area.

The composition of this invention can be applied from one to twelve times per day, either at diaper changes or incontinence pad changes and wound cleansings. The application rate will vary with the severity of the condition, the average length of exposure to irritants, and common practice procedures recommended by health care practitioners.

COMPONENTS OF INVENTION; ANTIMICROBIAL AGENT

Oxyquinoline, also known as 8-hydroxyquinoline, is a white or faintly yellow crystalline powder with a pleasant characteristic odor. Its chemical formula is $C_9H_7NO$. One gram of oxyquinoline dissolves in 1500 ml of water. It is freely soluble in alcohol, acetone, chloroform, benzene, and mineral acids Oxyquinoline is obtained by heating 0-aminophenol with O-nitrophenol, glycerol, and sulfuric acid. It has bacteriostatic, fungistatic, deodorant, and keratolytic properties. The oxyquinolines are contained in currently marketed products in concentrations of 0.06 to 2.5%.

Oxyquinoline has been known for its antimicrobial and antifungal qualities for decades. The drug itself has been on the market in the United States and Europe since 1906 and is widely used in several skin-related treatment protocols (Rohde et.al., 1986).

COMPONENTS OF INVENTION: SINGLE-DOSE APPLICATORS

In the methods of the present invention, any stability-tested and approved container, packette, applicator, or other such holding device may be employed to deliver a single dose of the aforementioned composition. The amount contained within the single-dose application may vary with the type of skin disorder, size of the affected area, and/or intensity of the condition. A suggested range might be approximately 0.2-0.5 ounces of substance per single dose application. Instructions for use of the composition would include that the user should dispose of the holding device immediately following dispensing of the composition to the affected area.

CLINICAL TESTING OF THE INVENTION

In order to test the safety and efficacy of this invention, a clinical study was conducted to compare the treatment protocol described in the invention with existing over-the-counter diaper dermatitis treatments (NOTE: two top market products were selected for the comparison study). Both of these products are only available in multi-use, reusable containers.

METHODOLOGY

A randomized double-blind trial was designed by the Biometrics Laboratory in the College of Medicine at the Ohio State University. Procedures for subject selection, randomization, data collection and rating of the rash were formalized in accordance with commonly accepted design principles. Sample size was calculated based on the ability to detect a large difference in the proportions showing improvement between groups. When the proportion of infants in the control group who showed improvement was 10%, then a sample size of 17 per group was needed to detect a 70% proportion showing improvement in the experimental treatment with a power of 95% and setting alpha at 0.05 (Fleiss, 1981).

Participants were solicited from licensed day-care facilities and from private homes in Columbus, Ohio from Jul. through Oct. 1989. Six large licensed facilities agreed to participate and signed parental consent was obtained prior to study participation.

At the beginning of each study day, in the centers and in the homes, the diapered area was examined by the research assistant. A five level grading scale was used to assess rash presence and severity (see FIG. 1). The diaper dermatitis grades reported are based on the perceptions of the degree of severity and extent of the rash as recorded by a trained observer. Grades of B or less (skin slightly pink to no rash evident) were not generally regarded as being diaper rash by the mothers. A minimum beginning rash level of grade C (skin pink with pimply areas) was considered necessary for inclusion in the study.

The study utilized a double-blind research design. The principal investigator randomized eligible infants into control versus treatment groups while the blinded research assistant determined rash levels. Information was gathered for all participants concerning preexisting skin disorders, use of medication, recent presence of diarrhea for 24 hours or more, birth date, race, gender, allergies, other health problems and type of diaper used. Infants with preexisting skin disorders or with active diarrhea were excluded from the study in order to control for possible confounding variables.

Each eligible child was randomized into either the control or experimental group. All caregivers were instructed by the principal investigator, a registered nurse, in proper technique for using and applying the selected substance. Caregivers for those in the experimental group were instructed in the use of an effective amount of non-irritating skin cleansing agent followed by the application process for the experimental substance. Caregivers for those in the control group were instructed to clean the diapered area using the current method and vehicles followed by the application process for the control substance (instructions for control substances were taken from manufacturer printed instructions on the product). A one ounce container of oxyquinoline containing ointment was provided for usage during the six hour time period (NOTE: since the time period for the study intervention was not long enough for growth of microbial agents in the experimental treatment container, a two to three application reusable container was employed for the study).

In all cases, the controls used either Desitin ® or A&D Ointment ® as the study treatment. In both groups, the principal investigator stressed the importance of keeping the research assistant blinded by instructing the caregiver to wash off the treatment and remove the diaper prior to the return visit of the research assistant for final grading.

Rashes were graded prior to treatment according to severity using a five level scale shown in FIG. 1. A post treatment measure of severity was obtained by the same observer after an interval of between five and nine hours. A change in rash severity was considered to have occurred only if a one grade or more difference was observed.

RESULTS

The results of this study overwhelmingly supported the effectiveness claims. A total of 34 infants were eligible for study, 17 were randomized into the experimental group and 17 into the control treatment group. The mean age was 12.5 months with 19 of the infants being male and 15 female. The majority of infants were white, although one subject in the experimental group was biracial. Only two study participants, one in each of the groups, was using antibiotics and only three of the 34 subjects (two in the control group and one in the experimental) used cloth diapers. No children in the study were being breastfed at the time of study. Five brands of disposable diapers were encountered during the study and no one brand was predominant in any group after randomization.

Characteristics of the study population are presented in Table 1. A comparison for possible differences between the experimental and control group with respect to gender (p=1.00), beginning rash level (p=0.92), and site of study being in-home or day-care (p=1.00) was performed. Chi-square or Fisher's exact test for dichotomous variables) revealed no statistically significant differences between groups (Fleiss, 1981). Independent sample t-tests were used to compare mean age and time interval between initial and final observation between treatment groups. No differences were found between groups for age (p=0.13) and observation time interval (p=0.64). Thus, the treatment groups were found to be similar with respect to basic characteristics.

Overall, two of the 17 control subjects improved at least one grade level while 13 of the 17 experimental subjects made at least the same degree of improvement.

In the control group, two participants had rashes which worsened one grade. In the experimental group one child had a two grade improvement and no children worsened.

Due to the small sample sizes, Fisher's exact test was used to compare the unadjusted proportions of infants who showed improvement. There was a dramatic difference with a larger number of children showing improvement in the experimental group, see FIG. 2.

TABLE 1

| | Characteristics of the Study Population Children with Diaper Dermatitis | | |
|---|---|---|---|
| | Control (Desitin or A & D) | Treatment (Oxyquinoline) | Total |
| Gender | | | |
| Male | 9 | 10 | 19 |
| Female | 8 | 7 | 15 |
| Mean Age in Months | 14.1 | 10.9 | 12.5 |
| (s.d.)* | (6.8) | (5.1) | (6.2) |
| Beginning Rash Level | | | |
| C | 5 | 5 | 10 |
| D | 7 | 6 | 13 |
| E | 5 | 6 | 11 |
| Study Site | | | |
| Home | 9 | 9 | 18 |
| Day-care | 8 | 8 | 16 |
| Mean Time from initial to final observation (in hours) | 6.2 | 6.0 | 6.1 |
| (s.d.)* | (0.8) | (1.0) | (0.9) |

*Standard Deviation

Ninety-five percent confidence intervals for the proportions were calculated for each of the treatments using the exact binomial distributions (Hollander & Wolfe, 1973). As presented in Table 2, the majority of the experimental group showed improvement (76.5%, 95% C.I.=50.1-93.2) whereas only 11.8% of the control group improved (95% C.I.=0.7-36.5) Individual group values are presented in Table 2. The proportion showing improvement in the experimental group versus the combined control group was significantly different (p<0.001).

A further comparison of the treatments for improvement was done by adjusting separately for possible confounding variables such as gender, beginning rash levels, place of study, age and observation time interval. Mantel-Haenszel chi-square test statistics (Pocock, 1983) were used to adjust the relative rates of improvement (ratios) for possible differences in the above confounders. This approach is valid for our sample sizes according to the criteria recommended by Mantel and Fleiss (Mantel & Fleiss, 1980). When adjusting for any of these variables, the experimental group still showed significantly higher improvement rates. The unadjusted relative risk was 6.5 (95% C.I.=2.4-17.3) for the probability of improvement for the experimental group relative to the control group. The adjusted ratios were similar to the unadjusted as seen in Table 3.

A further consideration was whether differences existed between the control treatments of Desitin ® and A & D Ointment. Desitin ® users (n=9) and A & D users (n=8) were compared separately to the experimental treatment.

TABLE 2

Comparison of Percentage Improvement of Diaper Dermatitis for the Oxyquinoline Treatment Group versus the A & D Ointment Group, Desitin Ointment Group and the Combined Control group of Desitin and A & D Ointment Users.

| | Number Tested | Number Improved | Percent Improved | P-Value* |
|---|---|---|---|---|
| Oxyquinoline | 17 | 13 | 76.5 | |
| Combined Control | 17 | 2 | 11.8 | <.001 |
| Desitin | 9 | 1 | 11.1 | .007 |
| A & D | 8 | 1 | 12.5 | .007 |

*Using Fisher's Exact Test to Compare each Control Treatment with Oxyquinoline

TABLE 3

Ratio of the Probability of Improvement for the Oxyquinoline Group Relative to the Combined Control Treatment Group, Adjusted for Other Variables.

| Adjustment Variable | Ratio of Improvement, Adjusted (95% Confidence Interval) |
|---|---|
| Gender | 6.6 (2.5, 17.6) |
| Beginning Rash Level | 6.7 (2.4, 18.7) |
| Care Location Home or Day-Care | 6.5 (2.4, 17.5) |
| Infant Age* | 7.9 (2.9, 21.6) |
| Observation Time Interval** | 7.1 (2.5, 20.3) |
| Unadjusted Ratio | 6.5 (2.4, 17.3) |

*Age was dichotomized into younger infants (less than 12 months) and older infants (12 months or older)
**Observation Time Interval was dichotomized into short (less than 6 hours) and long (6 hours or more).

No analysis was made comparing Desitin ® and A & D. No differences were seen for the experimental group versus Desitin ® or versus A & D users with respect to age, gender, beginning rash level, place of study and observation time interval. Percent showing improvement was also similar between the products with an 11.1% rate for Desitin ® and a 12.5% rate for A & D, values are shown in Table 2. The proportion showing improvement in the experimental group versus the Desitin group (p=0.003) and versus the A & D Ointment group (p=0.007) were shown to be different using Fisher's exact test. Stratified analysis was not possible due to the small sample sizes involved when considering brand-specific control treatments.

DISCUSSION

The experimental treatment consisting of an effective amount of non-irritating skin cleansing agent followed by the single dose application of a ointment containing oxyquinoline 0.22% was shown to have significantly greater proportions of infants demonstrating improvement in diaper rash than the control treatments of Desitin ® and A & D Ointments in a double-blind randomized clinical trial.

No side effects or worsening of the rash was seen in any of the experimental infants whereas two infants did experience a worsening rash using Desitin ®. Of the four infants in the experimental group who were not rated as showing any improvement, one in fact did improve. The particular infant had a beginning rash level of E and was considered to have the most severe rash encountered by the study group. Although the child did show marked improvement over the observation interval, it was not sufficient to be considered in a less severe rash category and was classified as a non-improvement.

Caregivers were frequently unaware of the importance of cleansing the diaper area as part of the diaper changing process, particularly when the diaper was merely 'wet' with urine. The fact that alcohol and fragrance containing wipes may further irritate infant skin was also not widely known. In addition, most of the popular over-the-counter diaper rash treatments do not contain sufficient antibacterial or antifungal agents and thus are not always effective once diaper dermatitis is present. Caregivers were not aware that these products are best used as preventive measures against diaper dermatitis rather than active therapy for a rash.

Despite vigilant preventive measures such as cleansing the diaper area with an effective amount of non-irritating skin cleansing agent, frequent changes and ointment use, diaper dermatitis may occur. It was therefore encouraging to find that, despite the small sample size, results of the trial demonstrate that the invention methodology of using an effective amount of non-irritating skin cleansing agent followed by the application of said invention in a single dose application form was superior in improving diaper dermatitis.

SUMMARY OF THE INVENTION

Diaper dermatitis is a major problem potentially affecting, but not limited to, any infant or young child who wears diapers. Most health care professionals concur that diaper dermatitis is a problem which, if left untreated, can have serious secondary sequelae. Additionally, the incidence of diaper dermatitis is grossly underreported. What is needed is a readily-available (e.g. over-the-counter) treatment methodology which is both safe and effective.

A review of the prior art in this area reveals that although other over-the-counter treatments are available, they:

1. are only most effective when used in the prevention of diaper dermatitis, not the treatment; and,
2. are of little value once the infant's skin has broken down and diaper dermatitis is evidenced; and,
3. are ineffective in combating a diaper dermatitis which is compounded by the presences of bacteria and/or fungus; and,
4. are frequently dispensed in multi-dose, reusable containers which render the product subject to contamination and could potentially worsen an existing case of diaper dermatitis; and,
5. are rarely used in conjunction with an effective cleansing methodology. In fact, it is extremely difficult to cleanse the infant's skin once these products have been applied.

The present invention encompasses methods and compositions for the topical treatment and irradication of diaper dermatitis and other skin-related diseases associated with (but not limited to) prolonged exposure to urine, feces, bacteria, or fungus. The methods and compositions act to provide effective treatment and irradication of diaper dermatitis by effectively cleansing the affected area in the aforementioned manner thereby preventing the action of the irritants against an infant's tender skin.

Following effective cleansing, a topical ointment, described in the preceding sections, is applied. The topical ointment uniquely combines chemical agents which are found to be most effective in the treatment of diaper dermatitis.

The unique approach described in the compositions and methods of this patent application offers many objects and advantages—especially compared to what is currently available on the market. Primarily, the objects and advantages include:

1. to provide a composition which is effective in the treatment of diaper dermatitis as demonstrated in a relevant clinical study;
2. to provide a composition which is effective as, but not limited solely to, a barrier against common irritants;
3. to provide a composition which is effective as, but not limited solely to, a skin conditioning agent;
4. to provide a composition which is effective in the treatment of diaper dermatitis which is complicated by bacteria and/or yeast infections;
5. to provide a method for more effective treatment of diaper dermatitis which includes proper cleansing with a specific type of cleansing agent followed by the application of an effective composition; and,
6. to provide a method for dispensing said compound in such a manner as to eliminate the potential for product contamination.

Although the description above contains many specificities, these should not be construed as limiting the scope of the invention, but as merely providing examples of some of the potential uses of this invention. For example, the methods/compositions of this invention could be used on other persons who may have to wear diapers such as an incontinent patient or a bed-ridden patient.

The embodiments of the invention in which exclusive property or privilege is claimed are defined as follows:

1. A method of treatment of human skin affected by diaper dermatitis and related skin disorders by topically applying to said affected areas an ointment consisting essentially of:
   a) about 49 percent by weight of petrolatum;
   b) about 15 percent by weight of lanolin;
   c) an effective amount of oxyquinoline to provide sufficient inhibition and inactivation of microbes present in said affected area to promote healing thereof; and
   d) an effective amount of one or more pharmaceutical carrier vehicles to promote topical application of said ointment without interfering with the effectiveness of the active agents which promotes healing of the affected areas, said carrier vehicles being taken from a group consisting of water, Beeswax, Sodium Borate, Methyl Salicylate, Sorbitan Sesquioleate, and Trisodium HESTA or mixtures thereof.

2. The method defined in claim 1 wherein said effective amount of oxyquinoline is about 0.22 percent by weight.

3. The method defined in claim 1 wherein the application of said ointment is preceded by cleansing the affected area with an effective amount of a non-irritating skin cleansing agent.

* * * * *